(12) United States Patent
Lachaine et al.

(10) Patent No.: US 8,135,198 B2
(45) Date of Patent: Mar. 13, 2012

(54) SYSTEMS AND METHODS FOR CONSTRUCTING IMAGES

(75) Inventors: Martin Lachaine, Montreal (CA); Ulrich Scheipers, Unterschleissheim (DE); Michael Donovan, Montreal (CA)

(73) Assignee: Resonant Medical, Inc., Quebec (CA)

( * ) Notice: Subject to any disclaimer, the term of this patent is extended or adjusted under 35 U.S.C. 154(b) by 736 days.

(21) Appl. No.: 12/186,801

(22) Filed: Aug. 6, 2008

(65) Prior Publication Data
US 2009/0041323 A1 Feb. 12, 2009

Related U.S. Application Data

(60) Provisional application No. 60/954,635, filed on Aug. 8, 2007.

(51) Int. Cl.
*G06K 9/00* (2006.01)
(52) U.S. Cl. ....................................................... 382/131
(58) Field of Classification Search .................. 382/128, 382/131
See application file for complete search history.

(56) References Cited

U.S. PATENT DOCUMENTS

| | | | |
|---|---|---|---|
| 3,082,322 A | 3/1963 | Koerner et al. |
| 3,777,124 A | 12/1973 | Pavkovich |
| 3,987,281 A | 10/1976 | Hodes |
| 3,991,310 A | 11/1976 | Morrison |
| 4,118,631 A | 10/1978 | Froggatt |
| 4,618,978 A | 10/1986 | Cosman |
| 4,882,741 A | 11/1989 | Brown |
| 4,923,459 A | 5/1990 | Nambu |
| 4,943,990 A | 7/1990 | Schar |
| 5,039,867 A | 8/1991 | Nishihara et al. |
| 5,080,100 A | 1/1992 | Trotel |
| 5,086,401 A | 2/1992 | Glassman et al. |
| 5,099,846 A | 3/1992 | Hardy |
| 5,107,839 A | 4/1992 | Houdek et al. |
| 5,117,829 A | 6/1992 | Miller et al. |
| 5,138,647 A | 8/1992 | Nguyen et al. |
| 5,207,223 A | 5/1993 | Adler |
| 5,222,499 A | 6/1993 | Allen et al. |
| 5,233,990 A | 8/1993 | Barnea |
| 5,291,889 A | 3/1994 | Kenet et al. |
| 5,295,483 A | 3/1994 | Nowacki et al. |
| 5,299,288 A | 3/1994 | Glassman et al. |
| 5,301,674 A | 4/1994 | Erikson et al. |
| 5,379,642 A | 1/1995 | Reckwerdt et al. |

(Continued)

FOREIGN PATENT DOCUMENTS

CA 2416887 2/2002

(Continued)

OTHER PUBLICATIONS

Besl et al., *A Method for Registration of 3d Shapes*, IEEE Transactions on Pattern Analysis and Machine Intelligence 14(2):239-256 (1992).

(Continued)

*Primary Examiner* — W. B. Perkey
(74) *Attorney, Agent, or Firm* — Goodwin Procter LLP (57) ABSTRACT

Techniques and systems for constructing a three-dimensional representations of anatomical structures from a series of images of the structure include creating interpolated images between actual images and defining voxels based on pixel values of the actual and interpolated images. A three-dimensional representation of the structure may be constructed based on the voxels.

20 Claims, 6 Drawing Sheets

U.S. PATENT DOCUMENTS

| | | | |
|---|---|---|---|
| 5,389,101 A | 2/1995 | Heilbrun et al. | |
| 5,391,139 A | 2/1995 | Edmundson | |
| 5,397,329 A | 3/1995 | Allen | |
| 5,408,101 A | 4/1995 | Wong | |
| 5,411,026 A | 5/1995 | Carol | |
| 5,438,991 A | 8/1995 | Yu et al. | |
| 5,442,675 A | 8/1995 | Swerdloff et al. | |
| 5,446,548 A | 8/1995 | Gerig et al. | |
| 5,447,154 A | 9/1995 | Cinquin et al. | |
| 5,483,961 A | 1/1996 | Kelly et al. | |
| 5,511,549 A | 4/1996 | Legg et al. | |
| 5,531,227 A | 7/1996 | Schneider | |
| 5,553,618 A | 9/1996 | Suzuki et al. | |
| 5,591,983 A | 1/1997 | Yao | |
| 5,603,318 A | 2/1997 | Heilbrun et al. | |
| 5,609,485 A | 3/1997 | Bergman et al. | |
| 5,673,300 A | 9/1997 | Reckwerdt et al. | |
| 5,690,108 A | 11/1997 | Chakeres | |
| 5,715,166 A | 2/1998 | Besl et al. | |
| 5,734,384 A * | 3/1998 | Yanof et al. | 345/424 |
| 5,740,225 A | 4/1998 | Nabatame | |
| 5,754,623 A | 5/1998 | Seki et al. | |
| 5,757,881 A | 5/1998 | Hughes | |
| 5,778,043 A | 7/1998 | Cosman | |
| 5,810,007 A | 9/1998 | Holupka et al. | |
| 5,836,954 A | 11/1998 | Heilbrun et al. | |
| 5,851,183 A | 12/1998 | Bucholz | |
| 5,859,891 A | 1/1999 | Hibbard | |
| 5,991,703 A | 11/1999 | Kase et al. | |
| 6,019,724 A | 2/2000 | Gronningsaeter et al. | |
| 6,038,283 A | 3/2000 | Carol et al. | |
| 6,094,508 A | 7/2000 | Acharya et al. | |
| 6,106,470 A | 8/2000 | Geiser et al. | |
| 6,112,341 A | 9/2000 | Moreland | |
| 6,117,081 A | 9/2000 | Jago et al. | |
| 6,119,033 A | 9/2000 | Spigelman et al. | |
| 6,122,341 A | 9/2000 | Butler et al. | |
| 6,129,670 A | 10/2000 | Burdette et al. | |
| 6,144,875 A | 11/2000 | Schweikard et al. | |
| 6,146,390 A | 11/2000 | Heilbrun et al. | |
| 6,198,957 B1 | 3/2001 | Green | |
| 6,208,883 B1 | 3/2001 | Holupka et al. | |
| 6,259,943 B1 | 7/2001 | Cosman et al. | |
| 6,269,143 B1 | 7/2001 | Tachibana | |
| 6,285,805 B1 | 9/2001 | Gueziec | |
| 6,292,578 B1 | 9/2001 | Kalvin | |
| 6,307,914 B1 | 10/2001 | Kunieda et al. | |
| 6,314,310 B1 | 11/2001 | Ben-Haim et al. | |
| 6,325,758 B1 | 12/2001 | Carol et al. | |
| 6,345,114 B1 | 2/2002 | Mackie et al. | |
| 6,359,959 B1 | 3/2002 | Butler et al. | |
| 6,366,798 B2 | 4/2002 | Green | |
| 6,385,286 B1 | 5/2002 | Fitchard et al. | |
| 6,385,288 B1 | 5/2002 | Kanematsu | |
| 6,390,982 B1 | 5/2002 | Bova et al. | |
| 6,405,072 B1 | 6/2002 | Cosman | |
| 6,423,009 B1 | 7/2002 | Downey et al. | |
| 6,438,202 B1 | 8/2002 | Olivera et al. | |
| 6,459,769 B1 | 10/2002 | Cosman | |
| 6,491,702 B2 | 12/2002 | Heilbrun et al. | |
| 6,511,430 B1 | 1/2003 | Sherar et al. | |
| 6,516,046 B1 | 2/2003 | Frohlich et al. | |
| 6,535,574 B1 | 3/2003 | Collins et al. | |
| 6,546,073 B1 | 4/2003 | Lee | |
| 6,553,152 B1 | 4/2003 | Miller et al. | |
| 6,560,311 B1 | 5/2003 | Shepard et al. | |
| 6,567,684 B1 | 5/2003 | Chenevert et al. | |
| 6,591,127 B1 | 7/2003 | McKinnon | |
| 6,600,810 B1 | 7/2003 | Hughes | |
| 6,621,889 B1 | 9/2003 | Mostafavi | |
| 6,628,983 B1 | 9/2003 | Gagnon | |
| 6,631,284 B2 | 10/2003 | Nutt et al. | |
| 6,636,622 B2 | 10/2003 | Mackie et al. | |
| 6,641,539 B2 | 11/2003 | Hirooka et al. | |
| 6,661,870 B2 | 12/2003 | Kapatoes et al. | |
| 6,662,036 B2 | 12/2003 | Cosman | |
| 6,669,635 B2 | 12/2003 | Kessman et al. | |
| 6,683,985 B1 | 1/2004 | Kase et al. | |
| 6,690,965 B1 | 2/2004 | Riaziat et al. | |
| 6,714,627 B1 | 3/2004 | Brown et al. | |
| 6,725,079 B2 | 4/2004 | Zuk et al. | |
| 6,728,424 B1 | 4/2004 | Zhu et al. | |
| 6,731,970 B2 | 5/2004 | Schlossbauer et al. | |
| 6,750,873 B1 | 6/2004 | Bernardini et al. | |
| 6,754,374 B1 | 6/2004 | Miller et al. | |
| 6,785,409 B1 | 8/2004 | Suri | |
| 6,804,548 B2 | 10/2004 | Takahashi et al. | |
| 6,914,959 B2 | 7/2005 | Bailey et al. | |
| 6,915,008 B2 | 7/2005 | Barman et al. | |
| 6,968,224 B2 | 11/2005 | Kessman et al. | |
| 6,980,679 B2 | 12/2005 | Jeung et al. | |
| 7,092,109 B2 | 8/2006 | Satoh et al. | |
| 7,095,823 B2 | 8/2006 | Topolnjak et al. | |
| 7,260,426 B2 | 8/2007 | Schweikard et al. | |
| 7,333,644 B2 | 2/2008 | Jerebko et al. | |
| 7,343,030 B2 | 3/2008 | Sawyer | |
| 7,430,321 B2 | 9/2008 | Okada et al. | |
| 7,438,685 B2 | 10/2008 | Burdette et al. | |
| 7,801,349 B2 | 9/2010 | Wang et al. | |
| 2001/0035871 A1 | 11/2001 | Bieger et al. | |
| 2001/0049475 A1 | 12/2001 | Bucholz et al. | |
| 2002/0018588 A1 | 2/2002 | Kusch | |
| 2002/0065461 A1 | 5/2002 | Cosman | |
| 2002/0082494 A1 | 6/2002 | Balloni et al. | |
| 2002/0087101 A1 | 7/2002 | Barrick et al. | |
| 2002/0122530 A1 | 9/2002 | Erbel et al. | |
| 2002/0156375 A1 | 10/2002 | Kessman et al. | |
| 2002/0176541 A1 | 11/2002 | Schubert et al. | |
| 2002/0183610 A1 | 12/2002 | Foley et al. | |
| 2002/0188194 A1 | 12/2002 | Cosman | |
| 2003/0018232 A1 | 1/2003 | Elliott et al. | |
| 2003/0028401 A1 | 2/2003 | Kaufman et al. | |
| 2003/0112922 A1 | 6/2003 | Burdette et al. | |
| 2003/0144813 A1 | 7/2003 | Takemoto et al. | |
| 2003/0153825 A1 | 8/2003 | Mooradian et al. | |
| 2003/0182072 A1 | 9/2003 | Satoh et al. | |
| 2003/0231790 A1 | 12/2003 | Bottema | |
| 2004/0015075 A1 | 1/2004 | Kimchy et al. | |
| 2004/0015176 A1 | 1/2004 | Cosman | |
| 2004/0034301 A1 | 2/2004 | Falco | |
| 2004/0092815 A1 | 5/2004 | Schweikard et al. | |
| 2004/0146137 A1 * | 7/2004 | Bruder et al. | 378/4 |
| 2004/0176925 A1 | 9/2004 | Satoh et al. | |
| 2004/0184646 A1 | 9/2004 | Oosawa | |
| 2004/0252870 A1 | 12/2004 | Reeves et al. | |
| 2004/0260142 A1 | 12/2004 | Lovoi | |
| 2005/0020917 A1 | 1/2005 | Scherch | |
| 2005/0180544 A1 | 8/2005 | Sauer et al. | |
| 2005/0251029 A1 | 11/2005 | Khamene et al. | |
| 2006/0020195 A1 | 1/2006 | Falco et al. | |
| 2006/0074292 A1 | 4/2006 | Thomson et al. | |
| 2006/0093205 A1 | 5/2006 | Bryll et al. | |
| 2006/0120608 A1 | 6/2006 | Luo et al. | |
| 2006/0241443 A1 | 10/2006 | Whitmore et al. | |
| 2006/0285641 A1 | 12/2006 | Scherch | |
| 2006/0293583 A1 | 12/2006 | Saracen et al. | |
| 2007/0015991 A1 | 1/2007 | Fu et al. | |
| 2007/0038058 A1 | 2/2007 | West et al. | |
| 2007/0055090 A1 | 3/2007 | Neustadter et al. | |
| 2008/0039713 A1 | 2/2008 | Thomson et al. | |
| 2008/0064953 A1 | 3/2008 | Falco et al. | |
| 2008/0219405 A1 | 9/2008 | Falco et al. | |
| 2008/0292194 A1 | 11/2008 | Schmidt et al. | |
| 2009/0003523 A1 | 1/2009 | Raanes et al. | |
| 2009/0093716 A1 | 4/2009 | Deischinger et al. | |
| 2009/0110145 A1 | 4/2009 | Lu et al. | |
| 2011/0069815 A1 | 3/2011 | Nord et al. | |

FOREIGN PATENT DOCUMENTS

| | | |
|---|---|---|
| CA | 2621741 A1 | 3/2007 |
| EP | 0647457 | 4/1995 |
| EP | 951697 A1 | 10/1999 |
| EP | 1304960 | 5/2003 |
| EP | 1426806 A2 | 6/2004 |
| EP | 1757228 A1 | 2/2007 |
| FR | 2778574 | 11/1999 |
| JP | 2006000220 | 1/2006 |

| WO | WO-992074 A1 | 1/1999 |
| --- | --- | --- |
| WO | WO-99/06644 | 2/1999 |
| WO | WO-99/26534 | 6/1999 |
| WO | WO-99/27839 | 6/1999 |
| WO | WO-0105316 A1 | 1/2001 |
| WO | WO-0209588 A1 | 2/2002 |
| WO | WO-03/076003 | 9/2003 |
| WO | WO-2006051523 A2 | 5/2006 |

OTHER PUBLICATIONS

Booth, *Modelling the impact of treatment uncertainties in radiotherapy*, University of Adelaide, Mar. 2002), Section 2.4 (<http://thesis.library.adelaide.edu.au/uploads/approved/adt-SUA20020816.175301/public/03chapter2.pdf>.

Brujic et al., *Analysis of Free-Form Surface Registration*, International Conference on Image Processing, pp. 393-396 (1996).

Cuisenaire, O., http://www.tele.ucl.ac.be/PEOPLE/OC/these/node74.html, Posted Oct. 5, 1999, Downloaded from the Internet on Aug. 10, 2004.

Cuisenaire, O., http://www.tele.ucl.ac.be/PEOPLE/OC/these/node75.html, Posted Oct. 5, 1999, Downloaded from the Internet on Aug. 10, 2004.

Cuisenaire, O., http://www.tele.ucl.ac.be/PEOPLE/OC/these/node12.html, Posted Oct. 5, 1999, Downloaded from the Internet on Aug. 10, 2004.

Dubois et al. Intraobserver and Interobserver Variability of MR Imaging- and CT-derived Prostate Volumes after Transperineal Interstitial Permanent Prostate Brachytherapy, Radiology. 207(3):785-9 (1998).

Eggert et al., *Simultaneous Registration of Multiple Range Views for Reverse Engineering*, International Conference of Pattern Recognition, pp. 243-247 (1996).

Hanks, et al., Three Dimensional Conformal External Beam Treatment of Prostate Cancer <http://prostate-help.org/download/pilgrim/10rad.pdf>.

Hanks et al., Clinical and Biochemical Evidence of Control of Prostate Cancer at 5 Years After External Beam Radiation, The Journal of Urology, vol. 154, 456-459 (1995).

Haralick et al., *Pose Estimation From Corresponding Data Point*, IEEE Transactions on Systems, Man, and Cybernetics, 19(6):1426-1446 (1989).

Hua et al., Development of a Semi-Automatic Alignment Tool for Accelerated Localization of the Prostate, Int. J. Radiation Oncology Biol. Phys., 55(3):811-823 (2003).

Jiang et al., *A New Approach to 3-d Registration of Multimodality Medical Images by Surface Matching*, SPIE vol. 1808 Visualization in Biomedical Computing,, pp. 196-213 (1992).

Krempien et al., Daily patient set-up control in radiation therapy by coded light projection, 3 pages.

Michalski et al., *Three-Dimensional Conformal Radiation Therapy (3DCRT) for Prostate Cancer*, Radiation Oncology Center, Mallinckrodt Institute of Radiology, Washington University Medical Center, St. Louis, Missouri (1996) <http://www.phoenix5.org/Infolink/Michalski/#3>.

Paskalev et al., Daily Target Localization for Prostate Patients based on 3-D Image Correlation, Phys. Med. Biol., vol. 49, pp. 931-939 (2004).

Pennec et al,. A Framework for Uncertainty and Validation of 3-D Registration Methods Based on Points and Frames, International Journal of Computer Vision 25(3), 203-229 (1997).

Pito, *A Registration Aid*, International Conference on Recent Advanced in 3D Digital Imaging and Modelling, pp. 85-92 (1997).

Pollack et al., Conventional vs. Conformal Radiotherapy for Prostate Cancer: Preliminary Results of Dosimetry and Acute Toxicity, Int. J. Radiation Oncology Biol. Phys., 34(3):555-564.

Robb, *Three-Dimensional Visualization in Medicine and Biology*, Book Chapter in: Handbook of Medical Imaging: Processing and Analysis, ed. Isaac N. Bankman, Academic Press, San Diego, CA, Chapter 42, pp. 685-71 (2000).

Robinson, *Advances in Multi-Modal Data Analysis: The Analyze Software Environment*, <http://www.ii.metu.edu.tr/~med-ii/makaleler/analyze_sw_enve.pdf>, 5 pages. Downloaded on Aug. 10, 2004.

Soffen E.M. et al. Conformal static field radiation therapy treatment of early prostate cancer versus non-conformal techniques: A reduction in acute morbidity. Int J Radiat Oncol Biol Phys, 24: 484-488 (1992).

Thayananthan, A. et al., <http://mi.eng.cam-ac.uk/~bdrs2/papers/thayananthan_cvpr03.pdf>, pp. 1-8. Downloaded from the Internet on Aug. 10, 2004.

Tome et al., Commissioning and Quality Assurance of an Optically Guided Three-dimensional Ultrasound Target Localization System for Radiotherapy, Med. Phys., 29(8):1781-1788 (2002).

Zhang, Iterative Point Matching for Registration of Free-Form Curves and Surfaces, International Journal of Computer Vision, 13(2):119-152 (1994).

<http://www.ucsf.edu/jpouliot/Course/chapter5.htm>.

<http://www.acmp.org/meetings/hershey_2001/highlights/benedict.pdf>.

<http://www.ucsf.edu/jpouliot/Course/Lesson22.htm>.

<http://www.gemedicalsystems.com/patient/see_treat/positioning.html>.

<http://www.emoryradiationoncology.org/high-technology.htm>.

<http://www.varian.com/pinf/imr000c.html>.

<http://www.ucsf.edu/jpouliot/Course/conformal_radiation_therapy.htm>.

Written Opinion of the International Search report for PCT/CA2005/001105 dated Oct. 27, 2005.

International Search Report for PCT/CA2005/01105 dated Oct. 27, 2005.

International Search Report for PCT/CA2005/001106 dated Nov. 15, 2005.

Written Opinion for PCT/CA2005/001106 dated Nov. 15, 2005.

International Preliminary Report on Patentability for International Application No. PCT/CA2005/001106 dated Jan. 23, 2007.

Written Opinion of the International Searching Authority for International Application No. PCT/CA2005/001106 dated Oct. 25, 2005.

International Search Report for PCT/CA2007/001626 dated Jan. 3, 2008 (4 pages).

Written Opinion of the International Searching Authority for PCT/CA2007/001626 dated Dec. 21, 2007 (7 pages).

International Preliminary Report on Patentability for PCT/CA2005/001428 dated Oct. 3, 2007 (1 page).

Written Opinion of the International Searching Authority for PCT/CA2005/001428 dated Nov. 8, 2005 (6 pages).

International Search Report for PCT/CA2007/000898 dated Jul. 12, 2007 (3 pages).

Written Opinion of the International Searching Authority fo PCT/CA2007/000898 dated Jul. 23, 2007 (6 pages).

International Search Report for PCT/CA2006/001289 dated Oct. 30, 2006 (3 pages).

Written Opinion of the International Searching Authority for PCT/CA2006/001289 dated Oct. 30, 2006 (6 pages).

Written Opinion of the International Searching Authority for PCT/CA2006/001461 dated Dec. 8, 2006 (5 pages).

International Search Report for PCT/CA2006/001461 dated Nov. 30, 2006 (5 pages).

Aoki, Y. et al. An Integrated Radiotherapy Treatment System and its Clinical Application, Radiation Medicine, vol. 5, No. 4, pp. 131-141, 1987.

Bijhold, J. et al. Fast evaluation of patient set-up during radiotherapy by aligning features in portal and simulator images, Phys. Med. Biol., 1999, vol. 36, No. 12, pp. 1665-1679.

Bijhold, J. Three-dimensional verification of patient placement during radiotherapy using portal images, Med. Phys. 20 (2), Pt. 1, Mar./Apr. 1993. pp. 347-356.

Boctor, et al., A Rapid Calibration Method For Registration and 3D Tracking Of Ultrasound Images Using Spatial Localizer, Proceedings of the SPIE (2003).

Boyer, A. A review of electronic portal imaging devices (EPIDs), Med. Phys. 19 (1), Jan./Feb. 1992 pp. 1.

Brunie L. et al. Pre-and intra-irradiation multimodal image registration: principles and first experiments, Radiotherapy and Oncology 29 (1993) pp. 244-252.

Claim Chart for Claim 10 of US Patent No. 5,447,154.

Cuadra, M.B. et al., Atlas-based Segmentation of pathological MR brain images using a model of lesion growth; Medical Imaging IEEE Transactions on, vol. 23, No. 10, pp. 1301-1314, Oct. 2004.

Czarnota G.J. et al. Ultrasound imaging of apoptosis: high-resolution non-invasive monitoring of programmed cell death in vitro, in situ and in vivo, British Journal of Cancer (1999) 81(3), pp. 520-527.

International Search Report and Written Opinion for PCT/CA2009/000750, mailed Sep. 18, 2009 (8 pages).

Leszczynski K W et al., "An Image Registration scheme applied to verification of radiation therapy" British Journal of Radiology British Inst. Radiol UK [Online] vol. 71, No. 844, Apr. 1998 (Apr. 1998), ISSN: 0007-1285, retrieved from the Internet: url:http://bjr.birjournals.org/cgi/reprint/71/844/413.pdf. [retrieved on Nov. 10, 2009].

Le Verre, C. et al. Intensity-Based Registration of Portal Images for Patient Positioning in Radiotherapy.

Lizzi, Frederic, et al., "Ultrasonic Spectrum Analysis of Tissue Assays and Therapy Evaluation," International Journal of Imaging Systems and Technology, Wiley and Sons, New York, vol. 8, No. 1, (Jan. 1, 1997), pp. 3-10.

Maurer C R et al., Registration of 3-D Images Using Weighted Geometrical Features, IEEE Transactions on Medical Imaging, IEEE Service Center, Piscataway, NJ, US vol. 15, No. 6, Dec. 1, 1996 (14 pages).

Meertens, H. et al. A method for the measurement of field placement errors in digital portal images, Phys. Med. Biol., 1990, vol. 35, No. 3, pp. 299-323.

Mencarelli, et al., "A Dosimetric Method to derive optimal couch corrections in the presence of anatomical deformations for H & N. cancer," abstract, 2011, 2 pages.

Nagel, et al., "Online dose-guided setup correction protocol for hypo fractionated lung radiotherapy," abstract, 2009, 1 page.

Reinstein, L. et al. Radiotherapy Portal Imaging Quality, Report of Aapm Task Group No. 28, American Association of Physicists in Medicine by the American Institute of Physics, New York, 1988.

Search Report for European Patent Application No. 06790638.8, mailed Apr. 23, 2010 (7 pages).

Simpson, R.G. et al. A 4-MV CT scanner for radiation therapy: The prototype system. Med. Phys. 9(4), Jul./Aug. 1982, pp. 574-579.

Supplementary European Search Report for PCT/CA2005001106_RNM-003PC_dated Nov. 10, 2009, 6 pages.

Supplementary European Search Report dated Oct. 25, 2010 (5 pages).

Supplementary Partial European Search Report for EP Application No. 5763463 dated Nov. 30, 2009, 7 pages.

Supplementary European Search Report dated Oct. 30, 2008 for European Patent Application No. 05788508.9/PCT/CA2005001428.

Swindell, W. et al. Computed tomography with a linear accelerator with radiotheraphy applications, Med. Phys. 10(4), Jul./Aug. 1983, pp. 416-420.

Troccaz, J. et al. Conformal external radiotherapy of prostatic carcinoma: requirements and experimental results, Radiotherapy and Oncology 29 (1993) pp. 176-183.

Troccaz., J et al. Patient Setup Optimization for External Conformal Radiotherapy, Journal of Image Guided Surgery, 1, pp. 113-120 (1995).

Van de Geijn, J. et al. A Graticule for Evaluation of Megavolt X Ray Port Films, Radiation Oncology Biology Physics, Nov. 1982, vol. 8, No. 11 pp. 1999-2000.

Zitova, B. et al., Image Registration Methods: A survey, Image and Vision Computing, Elsevier, Guildford, GB, vol. 21, No. 11, Oct. 1, 2003 (24 pages).

* cited by examiner

SYSTEMS AND METHODS FOR CONSTRUCTING IMAGES

CROSS-REFERENCE TO RELATED APPLICATIONS

This application claims priority to and the benefit of, and incorporates herein by reference, in its entirety, provisional U.S. patent application Ser. No. 60/954,635, filed Aug. 8, 2007.

TECHNICAL FIELD

This invention relates to methods and systems for constructing three-dimensional representations of anatomical features from a series of two-dimensional ultrasound slices.

BACKGROUND INFORMATION

Ultrasound imaging captures a time series of two-dimensional images (sometimes referred to as "frames") that each correspond to a position- and orientation-specific slice through an anatomical structure. The temporal nature of ultrasound scanning allows the operator to move the imaging device (typically a hand-held probe) to different positions and/or view angles to fully perceive the three-dimensional nature of the anatomical structure under study. The user may also decide to maintain a constant view angle and position in order to observe temporal changes in the anatomy itself due, for example, to breathing or heart beats.

Three-dimensional ultrasound images are useful because they provide a more complete representation of the anatomy for later review by a physician. They may also be used to direct or modify treatments during image-guided surgery or radiotherapy, for automated segmentation of an anatomical structure, and/or in combination with images obtained using other modalities such as computed tomography (CT) or magnetic resonance imaging (MRI). Conventionally, three-dimensional images consist of a series of voxels in space, with each voxel having color and luminance parameter values and a location in a defined coordinate system.

The most common type of three-dimensional ultrasound image acquisition (referred to as "freehand three-dimensional ultrasound") uses a two-dimensional probe. The operator sweeps the probe about the patient in the vicinity of the anatomical structure of interest, thus acquiring a time series of two-dimensional ultrasound frames. The frames may then be assigned positions and orientations in three-dimensional space by, for example, tracking the probe using an optical camera, a magnetic tracker, an articulated arm or robot, or by using various signal-processing algorithms on the images themselves to calculate the approximate motion of the probe between successive images. Three-dimensional probes are also available, but they tend to be more costly and have a limited field of view, and may be less flexible in imaging certain anatomical structures.

Many algorithms exist for creating three-dimensional voxel images from a series of two-dimensional freehand ultrasound images having known positions and orientations. Such techniques generally fall into one of two categories, namely "reverse" or "forward" techniques. Reverse techniques traverse each voxel and find the best parameter value(s) to assign to that voxel based on the adjacent pixels of the neighboring two-dimensional slices. The operation of determining which neighboring slices are relevant to a given voxel is time-consuming and costly. One example of the reverse approach is the voxel-nearest-neighbor (VNN) algorithm, in which each voxel is assigned the value of its nearest neighboring pixel. This method is relatively straightforward to implement, but the results tend to be visually unappealing and artifacts can appear in the reconstruction. To improve reconstructed images, some reverse algorithms compute an average of a number of pixels from neighboring slices to estimate mean parameter values for the voxel. This additional step, however, increases the computational cost.

One advantage of the reverse techniques is that they easily port to a multi-threaded processing environment. While each thread requires access to the original ultrasound image frames and their three-dimensional positions, the volume can be divided into several sub-volumes with each thread running on one of the sub-volumes. Another important advantage of the reverse techniques is that they can easily exploit optimizations typically found in modern processors. These allow large increases in speed if the jumps in memory access are small. By traversing the reconstruction volume voxel by voxel, the algorithm can utilize these processor optimizations by making the step between voxels consistent with a small jump in the computer memory.

In contrast, "forward" reconstruction techniques start with the first ultrasound frame and cycle through the pixels of that frame, while inserting the pixel values into the appropriate voxels. This process is then repeated for each frame. This approach is more straightforward than the reverse techniques because the algorithm only has to cycle through each pixel, find the correct voxel in three dimensions, and insert the pixel value at that voxel. If multiple pixels intersect a given voxel, their values are typically averaged, which results in the need for a separate volume in memory to keep track of the number of times a pixel "hits" a given voxel, and a larger word-width in the accumulation volume. One drawback of forward techniques is that if the maximum distance between successive frames is larger than the voxel size, voxels between the successive frames are not filled, resulting in "holes" in the reconstructed volume. This is typically addressed by a second step of the algorithm, referred to as "hole filling," which applies interpolation to fill the holes from neighboring voxel values. This second step slows down the reconstruction, and can lead to unappealing interpolation effects. Typically, a kernel size is defined for interpolation process. If the kernel size is too large, the result is excessive interpolation that results in a blurred image or artifacts; but if the kernel is made too small, some holes may remain unfilled.

Another drawback of forward methods is that they are not easily adapted to multi-threaded processing environments. This is because multiple memory volumes are needed to avoid interference among the multiple threads during the simultaneous writing of the voxels to memory; writing operations to the same fields at the same time by multiple threads is not possible. Furthermore, keeping multiple volumes in the memory at the same time increases memory costs dramatically. Also, pixels are added to the volume in an unorganized fashion, leading to large memory jumps. Thus, the forward algorithms do not take advantage of modern processor optimizations.

As such, existing reconstruction algorithms have disadvantages that lead to relatively slow processing times, unless sacrifices are made that compromise the reconstruction results. Therefore, a new approach to reconstruction is needed.

SUMMARY OF THE INVENTION

The present invention provides techniques and systems that facilitate the rapid acquisition of accurate, reconstructed three-dimensional ultrasound voxel data from a series of two-dimensional freehand ultrasound slices or one-dimensional scan lines having known positions and orientations in space. Embodiments of the invention involve two processing techniques, referred to herein as "frame interpolation" and "sorting." Although each is useful alone, certain embodiments use both to produce an accurate three-dimensional representation of an anatomical structure.

In a first aspect of the invention, "interpolated" slices are added in between previously obtained two-dimensional ultrasound slices such that the slices fill the reconstruction voxels directly without creating holes. In particular, a voxel space containing the image slices is defined; that is, the image slices intersect the voxel space and pixel values are used to determine the voxels they intercept. But because the distance between successive image slices exceeds the voxel size, voxels between the successive frames cannot be assigned values from intersecting image pixels. The artificial slices are used to supply pixel values to voxels not intercepted by image pixels, and are generated by interpolating pixels between adjacent neighboring image slices. As a result, the "hole filling" step found in many implementations of conventional reconstruction algorithms is no longer needed.

Accordingly, a method of constructing a representation of an anatomical structure uses two-dimensional images of the anatomical structure, and defines a voxel size for the anatomical structure (based, for example, on the average length of the voxel along each dimension). Interpolated images are then created between the pairs of acquired images such that all voxels between each pair are intersected by pixels from one of the original images or from an interpolated image. The number of required intervening slices, therefore, is determined by the distance between acquired images as compared with the voxel size. This process is repeated until each voxel can be assigned values based on intercepting pixel values. A representation of the anatomical structure is then constructed based on the voxels. For simplicity, the ensuing discussion refers to a unitary pixel or voxel "value," but it should be understood that the value may be unitary (or even binary, in the case of black-and-white images) or multidimensional (e.g., including hue, chroma and luminance values).

The images may be two-dimensional ultrasound images or, in some cases, one-dimensional image lines. In some embodiments, a reference coordinate system is defined about the anatomical structure. The reference coordinate system establishes the positions of the pixels and voxels relative to the structure. In certain implementations, the distance between pairs of images can be computed as the maximum (or in some cases average) distance between corresponding corner points of the two images.

In some embodiments, the technique further includes removing some of the previously-acquired ultrasound frames if, for example, they provide redundant information, or if they are not required to fill the reconstruction volume. For example, the frame rate of the ultrasound may be very high, leading to dense slice information relative to the voxel size, in which case removing certain slices reduces the number of slices that must be processed for reconstruction without adversely affecting image quality.

In further embodiments, the slices may be subdivided into a number of sub-images, which can reduce the number of inserted slices and/or increase the number of images that can be removed. The process of subdividing the images may be particularly applicable in instances where the acquired ultrasound slices are not parallel, as is usually the case in freehand three-dimensional ultrasound.

In some cases, the voxel can be defined using the pixel values stored in a computer memory. For example, a reference coordinate system can be defined about the anatomical structure and lines can be determined that intersect a plane substantially orthogonal to a first axis of the reference coordinate system and the images and interpolated images that intersect the voxel. Using the number of points along each intersection line to define an array for each intersection line, pixel values from each point along each intersection line are placed into the respective position of the respective array. This process can be repeated for subsequent planes along the first axis, and once a certain number of planes are processed, a three-dimensional representation of the anatomical structure is created based on the pixel values stored in the arrays.

In another aspect, a method for constructing a three-dimensional representation of an anatomical structure from a series of images (e.g., two-dimensional ultrasound images) includes defining a reference coordinate system about the anatomical structure and determining intersection lines between a plane substantially orthogonal to a first axis of the reference coordinate system and the images. For each intersection line, an array is defined based on equally spaced points along the intersection line, and the pixel value at each point is placed into the corresponding position of the array. This process can be repeated for subsequent planes along the first axis, and once a the number of planes processed is sufficient to create an accurate representation of the anatomical structure, a three-dimensional representation of the anatomical structure is created based on the pixel values stored in the arrays. In some cases, the number of planes processed may be limited by processing capabilities and/or time constraints.

In some embodiments, an average pixel value may be calculated for each intersection line based on the pixel values along that line, and voxels along the intersection line may be defined based on the average pixel value.

In another aspect, a system for constructing a voxel-based representation of an anatomical structure includes a register, a processor and a display. The register stores images of the anatomical structure, which may be received from one or more imaging modalities. The processor is configured to define a space of sized voxels representing the anatomical structure and to determine distances between the images stored on the register. The processor is also configured to create interpolated images between the stored images based on the inter-image distances and the voxel size such that a sufficient number of voxels between the images are intersected by pixels from at least one stored or interpolated image. Pixel values are then assigned to the voxels based on the pixels that intersect the respective voxels. The display presents a three-dimensional representation of the anatomical structure constructed from voxels.

In some embodiments, the processor may be further configured to subdivide the images into a number of sub-images, which may reduce the number of inserted slices and/or increase the number of images that can be removed.

The foregoing and other objects, features and advantages of the present invention disclosed herein, as well as the invention itself, will be more fully understood from the following description of preferred embodiments and claims, when read together with the accompanying drawings.

BRIEF DESCRIPTION OF THE DRAWINGS

In the drawings, like reference characters generally refer to the same parts throughout the different views. Also, the drawings are not necessarily to scale, emphasis instead is generally being placed upon illustrating the principles of the invention.

DETAILED DESCRIPTION

Figure 1:
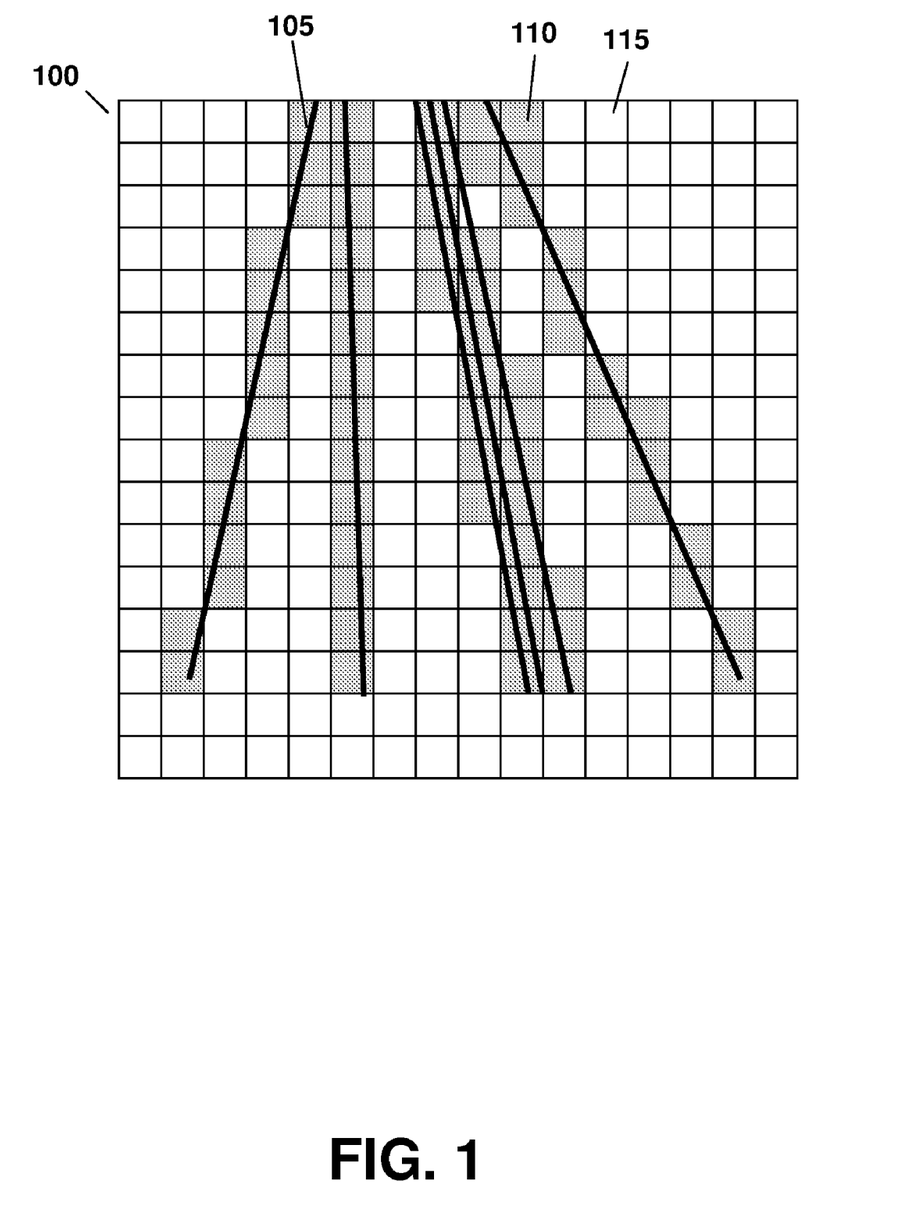
FIG. 1 is a sectional schematic showing ultrasound slices as inserted into a three-dimensional voxel grid or space using prior art techniques.

FIG. 1 shows a three-dimensional voxel grid or space 100 as a two-dimensional section for illustrative purposes. A series of two-dimensional ultrasound slices 105, each having positional and orientation information relative to the voxel space 100, has been projected therein. Each slice 105 intercepts a roughly two-dimensional region of voxels (the deviation of the intercepted region from perfect planarity increasing with the degree to which the interception angle is off-axis). Using conventional techniques, each voxel is "filled" by assigning a value based on the pixels from the slice or slices 105 that intercept the voxel. The voxels that may have values assigned in this way are illustrated as gray squares 110, whereas the white squares 115 (representing "holes") cannot draw values from intercepting slices 105, and would typically be filled in a second processing step. Embodiments of the invention address the problem of filling voxels intercepted by the ultrasound slices as well as some or all of the voxels through which no ultrasound slices pass. As a result, an accurate and computationally efficient three-dimensional representation of an anatomical structure can be created. It should be understood, however, that although the ensuing discussion involves two-dimensional image slices, the invention can also be employed using one-dimensional linear images.

Figure 2:
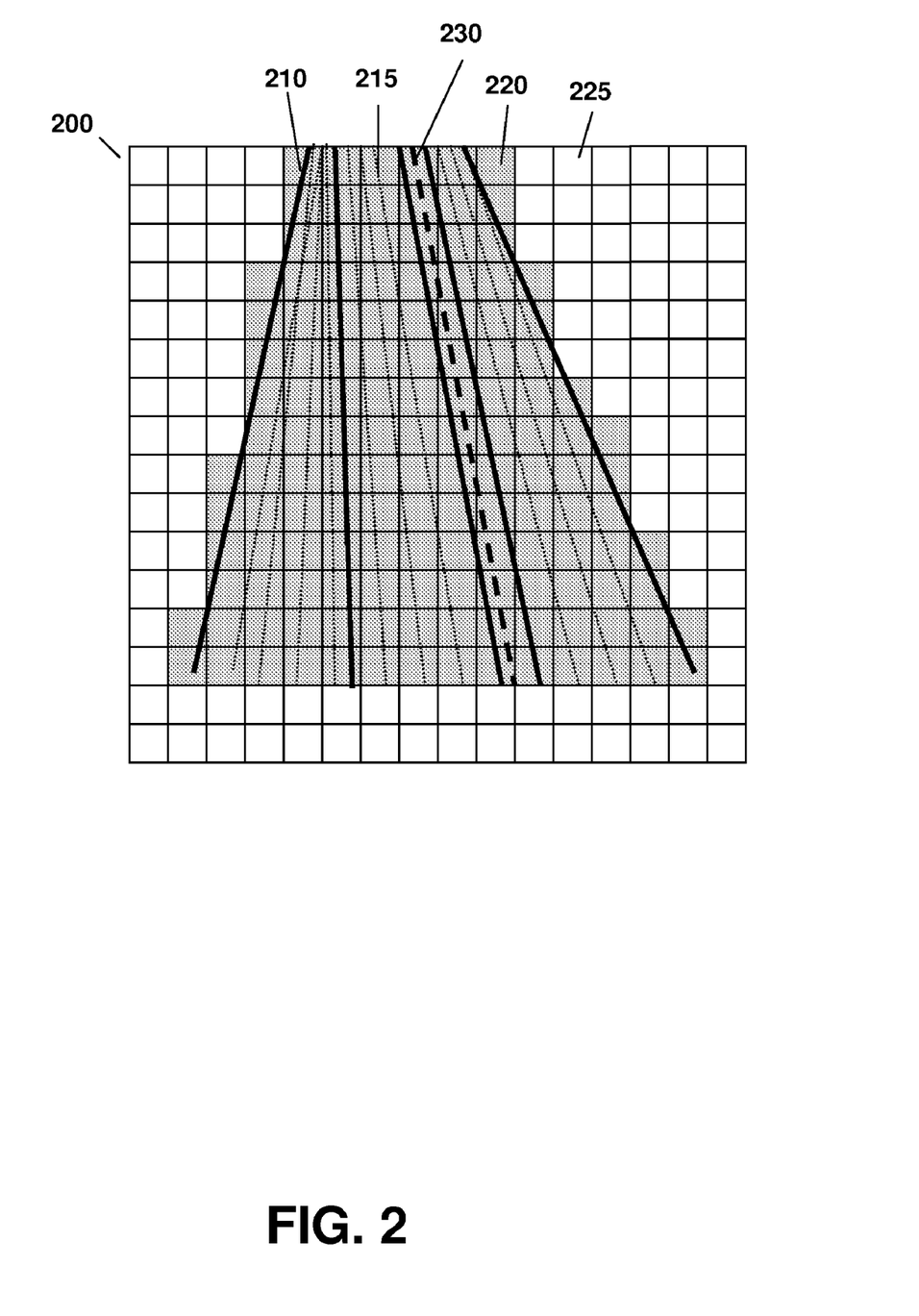
FIG. 2 illustrates the original ultrasound slices of FIG. 1, interpolated ultrasound slices as inserted into the voxel grid, and the removal of original slices.

Referring now to FIG. 2, the spacing between "original" slices 210 can be computed to determine if any of the original slices are close enough to each other (e.g., within some defined threshold) to fill all of the empty voxels between the slices. This obviously depends on the density of the slices 210 relative to the density of the voxels in the space 200. For voxels not intersected by an original slice 210, one or more interpolated slices 215 can be added between the original slices 210 to provide pixels whose values are used to fill the remaining voxels. Voxels lying outside the region of interest may be ignored, and these remain white in FIG. 2. In some embodiments, if certain original slices are so close that they do not contribute additional information to the voxels—i.e., they redundantly intercept voxels already intercepted by other slices—they can be removed, as shown at 230.

Figure 3:
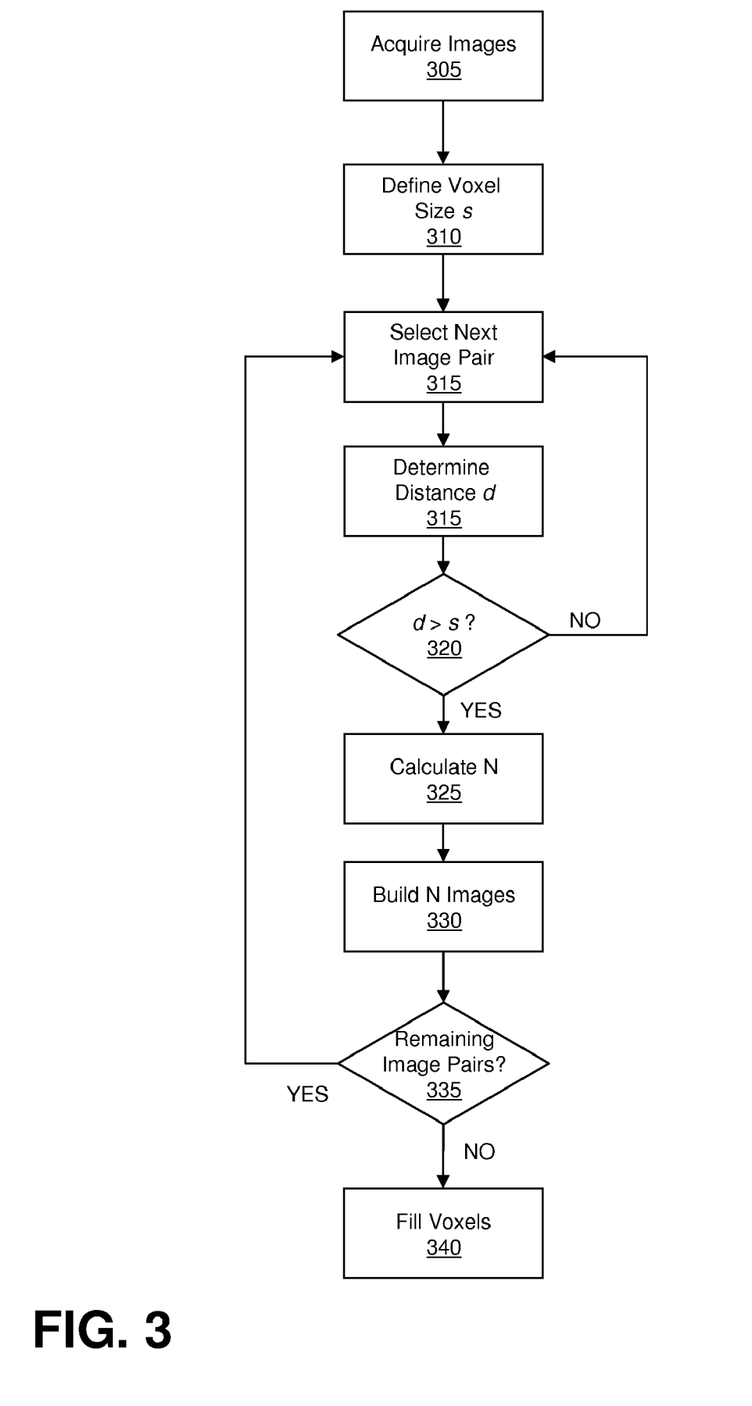
FIG. 3 is a flow chart illustrating steps for constructing a three-dimensional representation of an anatomical structure according to one embodiment of the invention.

FIG. 3 illustrates a representative sequence of steps for constructing a three-dimensional representation of an anatomical structure under study. A series of images is obtained (STEP 305) using, for example, a two-dimensional ultrasound imaging system. The images may be obtained directly from an ultrasound probe as it is scanned about a patient, or received from memory of a data storage device. A voxel size s is defined (STEP 310) based, for example, on parameters such as the structure under study, the proposed treatment, computational capacity and/or the imaging modality used to take the initial images. The voxel size may be used as a determining factor as to whether any given pair of acquired images are "close" enough to each other (e.g., there are no voxels between the images that are not intercepted by an image slice) such that pixel values from the actual images may be used to define all voxels between them. An image pair is selected (STEP 315) and the distance d between the two images is determined (STEP 320), as described in greater detail below and with reference to FIG. 4. If d>s (i.e., if a voxel can fit between the two image slices without being intersected), then one or more intervening, interpolated slices will be defined, and the required number of interpolated slices is calculated (STEP 325). If d<s, another image pair is selected. The interpolated images are built (STEP 330) based on pixel values in neighboring (actual or interpolated) images and interposed between the actual images. The method continues, progressing through each image pair (STEP 335) until all the slices are traversed and a set of slices intercepting all empty voxels is obtained (STEP 340). Voxel values within the space bounded by the first and last actual image slice are defined based on the pixel values of the actual and interpolated images, thus constructing a three-dimensional representation of the anatomical structure. For example, the spacing between slices 1 and 2 may result in the addition of three interpolated slices, between 2 and 3 two slices may be required, and between 3 and 4 no slices are required. Further, the spacing between slice 4 and 5 may allow for the removal of slice 4 while still having every voxel intersected.

Figure 4:
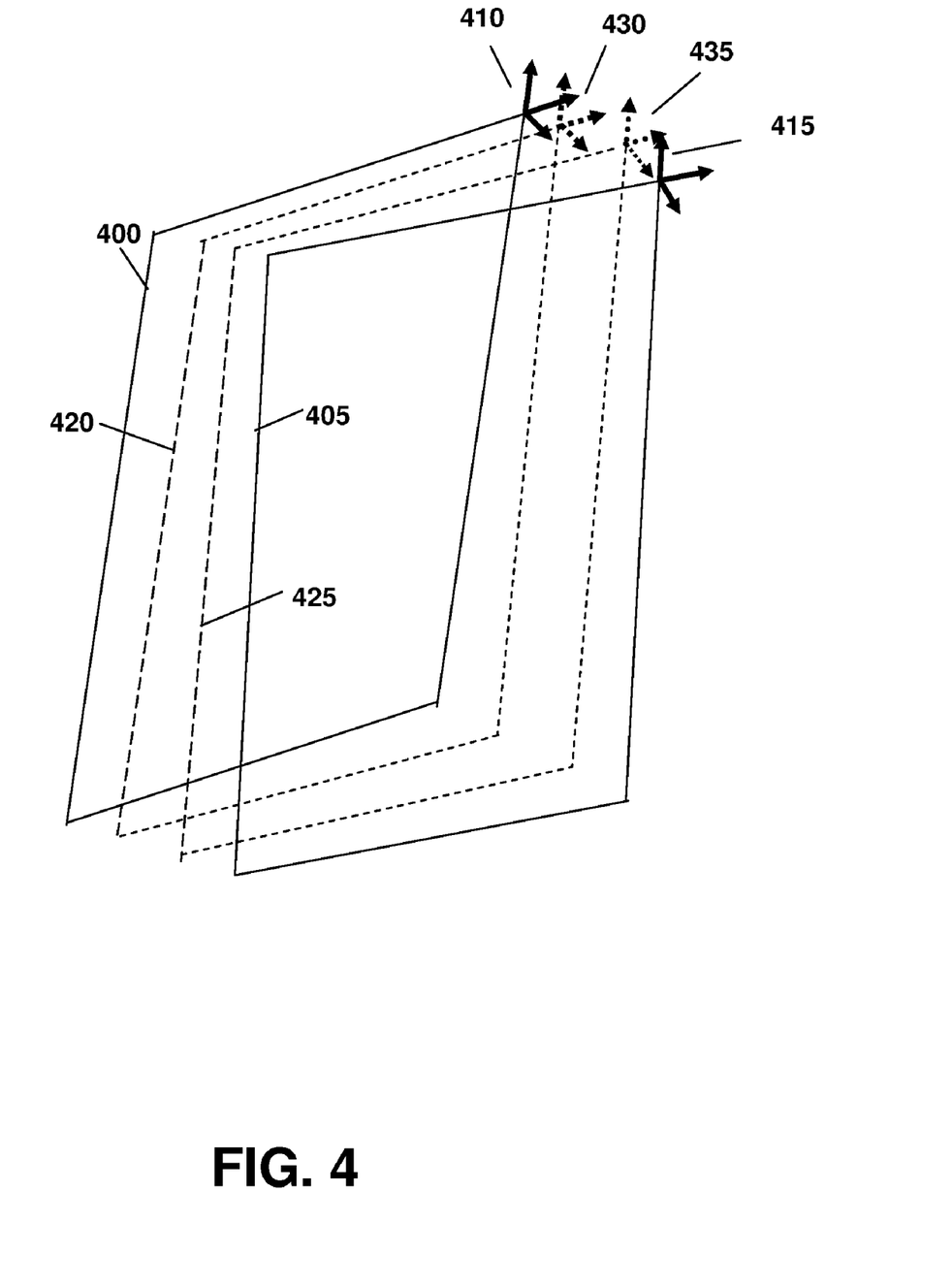
FIG. 4 schematically illustrates original frames and interpolated frames and associated transformations based on a three-dimensional coordinate system.

Referring to FIG. 4, the positions of the image slices may be established relative to one or more coordinate systems. For example, the coordinate systems may be defined by quaternion values $q_0$, $q_x$, $q_y$, $q_z$ and translational values $t_x$, $t_y$, $t_z$ relative to another coordinate system, such as one defined by the room coordinates or a tracking system. Components of the translations can be linearly interpolated in a manner similar to the image slices above, so long as the quaternion values are renormalized after interpolation. Quaternions can also be interpolated using other techniques such as spherical linear interpolation ("slerp"). If the coordinate systems are defined in terms of matrices, they may be converted to quaternions prior to interpolation, and the interpolated quaternion can be converted back into a matrix. In some embodiments, the coordinate systems may be defined in terms of Euler angles, in which case the consistency of the angle definitions must be maintained.

FIG. 4 shows the outline of two "original," adjacent slices 400, 405 (individual pixels are not shown for clarity), with corresponding coordinate systems 410, 415 defined by the positional and rotational information needed to calculate the positions of each pixel within the slices in three-dimensional space. The values can be acquired, for example, by using a camera-based tracking system that tracks markers disposed about (e.g., affixed to the handle) of an ultrasound probe as the images are acquired. The camera system outputs the positional and rotational values of the markers, which through calibration or other techniques can be related to an absolute coordinate system such as that of a room. In the absence of a tracking system, approximate positional and rotational values can be found by analyzing the difference in pixel values of neighboring slices, and estimating the displacement based on, for example, the speckle correlations between the two images. Also, magnetic tracking systems or mechanical systems, such as articulated arms or robots, can be used to acquire position information. Although no absolute coordinate system exists in this case, an arbitrary coordinate system can be defined.

Still referring to FIG. 4, a distance measure between the two image frames 400, 405 may be calculated, in one example, by finding the positional difference between the four corners of the two images, and using the maximum of these four corner-to-corner distances as the distance measure d. The distance measure d may then be compared to the initially defined voxel size s, which is usually the same (or close to the same) size in each direction (i.e., along each side of the voxel). In some embodiments, the voxel size s includes three components, one in every direction of the voxel's three-dimensional volume and any one of, or an average of the three components may be used. If $d \leq s$, the two slices are close enough to fill all the voxels between them without creating holes. Furthermore, original slices may be removed as long as the condition $d \leq s$ still holds. If $d > s$, however, some number N of interpolated slices may be required. In one embodiment, the number of interpolated slices N to be added is determined by ceil(d/s), where the ceil ("ceiling") operation refers to the nearest higher integer to its argument. For example, if d/s=2.6, ceil(d/s)=3, and therefore three interpolated slices are added. This technique ensures that all (or substantially all) of the voxels between the slices are filled. In one embodiment, empty voxels at the corners of the volume can be accepted (e.g., remain unfilled) in order to reduce the processing burden, assuming the resulting loss in image quality is acceptable. In such cases, a reduction factor f may be used, thereby modifying the formula for N to ceil(fd/s)). Suppose N slices are to be added between two slices whose pixel values are defined by matrices A(u,v) and B(u,v). In one embodiment, interpolated slices $C_i(u,v)$ (where i=1 ... N) can be created by performing a linear interpolation of each pixel, e.g. $C_i(u,v) = f_i A(u,v) + (1-f_i) B(u,v)$ where $f_i = i \times d/(N+1)$. Higher-order interpolation, i.e., interpolation based on more than two neighboring slices, may be used as well, although the marginal improvements in image quality may become small when compared to the extra computational burden imposed by the additional constraints.

In some embodiments, a maximum distance threshold D between original slices may limit the creation of interpolated slices to avoid interpolation over very large distances (e.g., where d>D), as it is likely that any reconstructed voxel information in such cases would not be useful or accurate. In still other embodiments in which slices are removed due to an excess of slices through one or more voxels, the pixel values for the removed slices may be averaged and assigned to the voxels.

Once pixel values of interpolated slices 420, 425 are found (and coordinates assigned based on the associated coordinate systems 430 and 435), the process may be repeated for the next two consecutive slices, and so on until each of the slices has been addressed. At the end of the procedure, three-dimensional image reconstruction is based on the actual and interpolated image slices, thus assuring there are no holes in the reconstruction.

In some instances, the slice interpolation and removal techniques described above may not be optimal—that is, more slices may be added than are needed to ensure that all voxels are filled. For example, if original ultrasound images were acquired using a fanning motion (e.g., where one end of the probe remains relatively stable while the other end traces an arc about the stable end) a greater number of interpolated slices will be needed to fill voxels at certain portions of the reconstruction than others. In such cases, each image frame may be separated into an array of sub-images. For example, if each slice is 200 pixels square (i.e., 200×200), each image may be converted to a set of four sub-images, each 100 pixels square (i.e., 100×100 pixels). These sub-images can then be used to create interpolated slices, remove redundant slices, and reconstruct the final three-dimensional voxel image.

In some instances, interpolation is carried out based on one-dimensional lines instead of two-dimensional images. In such cases, a minimum line length needed to fill the volume without leaving empty voxels can be calculated from the size of the voxels and the coordinates of the lines. The lines may then be interpolated and/or resampled to a length close to the minimum length. For example, an ultrasound system may provide raw data lines having a length of 2000 samples for each line. According to the selected voxel size, the selected coordinate system of the three-dimensional volume, and the positions of the one-dimensional ultrasound lines, the minimum length of a line required may be determined to be 800 pixels. In such cases, downsampling the line by a factor of two provides lines 1000 pixels in length, close to the required 800 pixels.

The above techniques ensure that no holes exist when reconstructing directly from a series of ultrasound slices, and also that the optimal number and spacing of slices is present prior to the reconstruction step. The new set of slices can then be used to reconstruct a voxel image using the sorting method described below.

More specifically, the original and/or interpolated slices may be used to construct a three-dimensional voxel-based image of an anatomical structure by filling the voxels of the image with original and interpolated slices. In one such approach, referred to here as the sorting method, a pre-defined image coordinate system defines the voxels' positions in three-dimensional space, and a subset of pixels from the ultrasound slices corresponding to a tolerance band around a given [x, y] position in a plane of the image coordinate system is determined for each ultrasound slice (either original or interpolated). This subset of pixels is then inserted into the voxels intersected by the respective plane of the image. The process can be repeated for different [x, y] bands along the z axis of the image coordinate system, until all voxels have been addressed. In this manner, the pixels are inserted into the reconstruction grid in an order that minimizes jumps in the reconstruction volume, and thus in memory. The result is generally much faster and more efficient than either forward or reverse methods, and particularly in combination with the interpolation technique described above with reference to FIGS. 3 and 4, provides very accurate reconstructed images.

The interpolation and sorting methods may be used independently, but when used together address the disadvantages of both the reverse and forward techniques. The slices can be inserted into the volume without filling holes after insertion and the pixels can be efficiently and rapidly inserted into the volume in a manner that takes advantage of processor optimizations by limiting the insertions along a single dimension of the volume.

Figure 5:
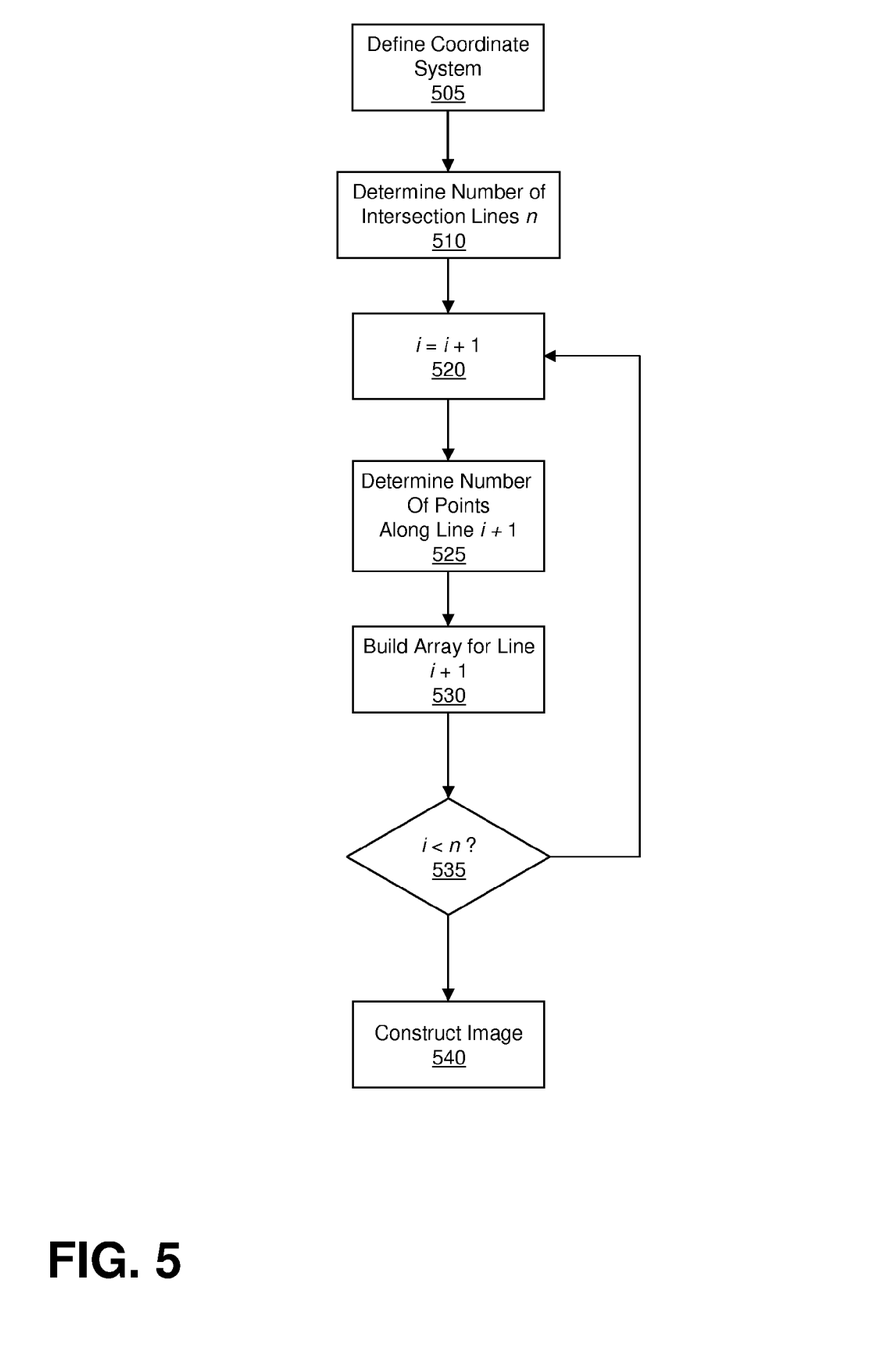
FIG. 5 is a flow chart illustrating steps for constructing a three-dimensional representation of an anatomical structure from a series of image slices according to one embodiment of the invention.

Referring now to FIG. 5, each two-dimensional slice, which may or may not have been created using the interpolation method described above, corresponds to a set of pixels each having a location in three-dimensional space based on the coordinate system transformation applied to the slice in which the pixel lies. A reconstruction coordinate system may be defined (STEP 505), for example, as having x, y, and z components and voxels defined relative to the reconstruction coordinate system using the coordinate system transformation. The voxels reside in the memory of a computer. In an embodiment, the memory stores the voxels in succession, but in a manner such that voxel jumps along one of the axes (the z axis, for example) results in a unit jump in memory, whereas jumps along other axes (the x axis and the y axis) result in memory jumps greater than one unit ("far" jumps). Because unit jumps can be performed much faster than far jumps, the volume can be filled much faster if only unit jumps are needed to fill all of the voxels.

Once the positional values of the slices are determined, the transform between each image slice and the target volume can be calculated, as well as an intersection line between each image and the z=0 plane of the target volume and the translation of the intersection line for increments along the z axis.

The target volume can then be filled slice-by-slice along the z-plane. For each z-plane, one or more intersection lines are determined for each image (STEP 510), and a counter used (STEP 520) to track the processing of each intersection line. The coordinates for the first and last point of the intersection line are calculated for each image. The number of points between the first point and the last point may be calculated (STEP 525) for each intersection line, and the unit transformations for any point along the intersection lines can be calculated as well. Because increments are mainly conducted in the direction of the volume that allows unit jumps instead of far jumps, the filling of the volume is accomplished much faster than by traditional techniques.

The z-planes are then filled along the y axis. Accumulation arrays of length x are allocated in memory to store the pixel values. The value of every point crossing the y position of the accumulation array or intersection line can then be added to the x index of the accumulation array for every image (STEP 530), and the number of accumulated values is stored for further processing. If additional lines remain, the process repeats (STEP 535) until all lines are addressed. The unit translations (described above) may then be applied to each of the point positions. The values within the accumulation array may then be divided by the number of accumulated values and associated with the target volume, and the target volume will therefore be filled with the mean or average values of the pixels (STEP 540). Such an approach may, for example, be used to complete the filling and construction step (STEP 340) of FIG. 3.

Other pixel selection and calculation techniques such as the maximum pixel value, the first encountered pixel value, the last encountered pixel value, or other more complex functions of the underlying pixel values may instead be used.

In some embodiments, the process can be summarized according to the following steps:
(a) obtain a series of input image slices having pixel values (u,v);
(b) define a coordinate system that determines the position of each voxel;
(c) calculate the positions of the pixels in the defined coordinate system;
(d) choose a subset of pixels whose x,y positions lie within a predetermined tolerance band;
(e) define the values of voxels lying within the tolerance band based on the subset of pixels corresponding thereto; and
(f) repeat with pixels having different x,y values until the voxel grid is filled.

Figure 6:
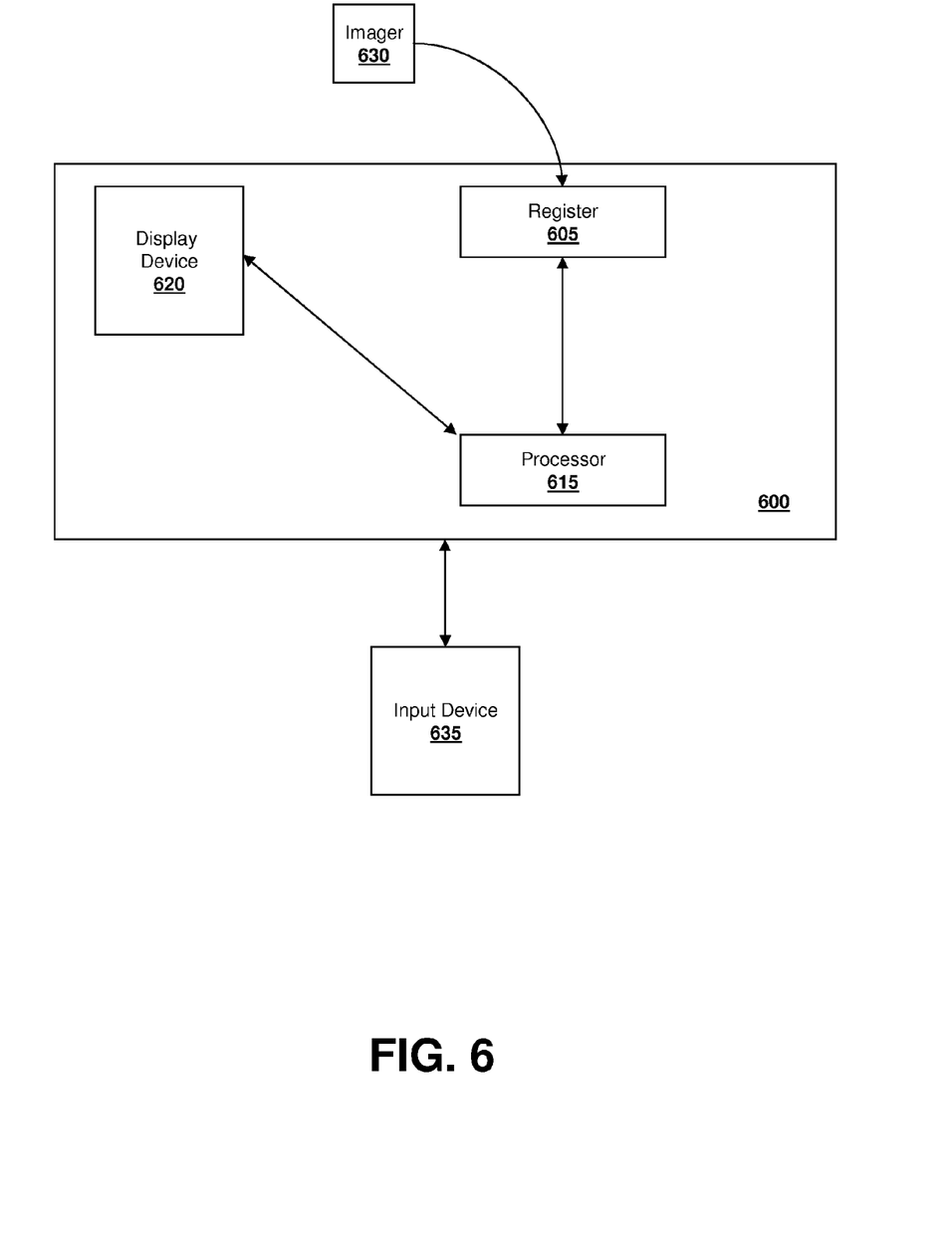
FIG. 6 is a schematic representation of a system in accordance with an embodiment of the invention.

FIG. 6 schematically depicts a hardware embodiment of the invention realized as a system 600 for constructing a three-dimensional representation of an anatomical structure based on previously-acquired ultrasound images. The system 600 comprises a register 605, a processor 615, and a display 620.

The register 605, which may be any suitably organized data storage facility (e.g., partitions in RAM, etc.), stores images received from an imager 630 such as an MRI, CT/PET scanner, ultrasound device, or x-ray device. In some embodiments, the images are stored on a data-storage device separate from the imager (e.g., a database, microfiche, etc.) and sent to the system 600. The images may be received through conventional data ports and may also include circuitry for receiving analog image data and analog-to-digital conversion circuitry for digitizing the image data.

The register 605 provides the image to the processor 615. The processor 615 implements the functionality described above, namely defining a voxel size for the anatomical structure, determining distances between image pairs and comparing the distance to the voxel size, and creating the interpolated images. Further, the processor 615 is configured to construct the three-dimensional representation of the anatomical structure based on the defined voxels. The processor 615 may be implemented in hardware or software, or a combination of both on a general-purpose computer. In addition, such a program may set aside portions of a computer's random access memory to provide control logic that affects one or more of the image capture, processing, user manipulation (using, for example, an input device 635) and/or presentation on the display 620. In such an embodiment, the program may be written in any one of a number of high-level languages, such as FORTRAN, PASCAL, C, C++, C#, Java, Tcl, or BASIC. Further, the program can be written in a script, macro, or functionality embedded in commercially available software, such as EXCEL or VISUAL BASIC. Additionally, the software can be implemented in an assembly language directed to a microprocessor resident on a computer. For example, the software can be implemented in Intel 80x86 assembly language if it is configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

While the invention has been particularly shown and described with reference to specific embodiments, it should be understood by those skilled in the area that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method of constructing a voxel-based representation of an anatomical structure, the method comprising the steps of:
   (a) acquiring a plurality of images of the anatomical structure;
   (b) defining a space of voxels, each having a size, with respect to the acquired images;
   (c) determining distances between the acquired images;
   (d) based on the determined distances and the voxel size, creating a sufficient number of interpolated images between the acquired images such that a sufficient number of voxels between images are intersected by pixels from at least one acquired image or interpolated image; and
   (e) assigning values to the voxels based on the intersecting pixels.

2. The method of claim 1 wherein the images comprise or consist of two-dimensional ultrasound images.

3. The method of claim 1 wherein the images comprise or consist of one-dimensional image lines.

4. The method of claim 1 further comprising defining a reference coordinate system about the anatomical structure and aligning the reference coordinate system to the voxel space and the acquired images.

5. The method of claim 4 wherein the distance between two images is the maximum distance between corresponding corner points of the two images based on the reference coordinate system.

6. The method of claim 1 wherein the voxel size corresponds to an average length of the voxel along each of three dimensions.

7. The method of claim 1 further comprising removing one or more of the acquired images such that all voxels are intersected by no more than one image.

8. The method of claim 1 further comprising creating two or more sub-images from each image in the series and performing steps (c) through (e) using the sub-images.

9. The method of claim 1 wherein the sufficient number of voxels comprises all of the defined voxels.

10. The method of claim 1 further comprising:
(i) defining a reference coordinate system about the anatomical structure;
(ii) determining a plurality of intersection lines between a first plane substantially orthogonal to a first axis of the reference coordinate system and the acquired images and the interpolated images intersecting each voxel;
(iii) determining a number of points along each intersection line;
(iv) defining an array for each intersection line having a number of positions based on the number of points in its respective intersection line;
(v) placing pixel values from each point along each intersection line into the respective position of the respective array;
(vi) repeating steps (ii) through (v) for subsequent planes along the first axis; and
(vii) constructing a three-dimensional representation of the anatomical structure based on the pixel values stored in the arrays.

11. A method of constructing a three-dimensional representation of an anatomical structure from a series of images, the method comprising:
(a) defining a reference coordinate system about the anatomical structure;
(b) determining a plurality of intersection lines between a first plane substantially orthogonal to a first axis of the reference coordinate system and an image from the series of images;
(c) for each intersection line, defining an array having a number of positions based on a length of the intersection line;
(d) placing pixel values from each position of each intersection line into respective positions in the corresponding arrays;
(e) repeating steps (b) through (d) for additional planes along the first axis; and
(f) constructing a three-dimensional representation of the anatomical structure based on the pixel values stored in the arrays.

12. The method of claim 11 wherein the series of images comprises two-dimensional ultrasound images.

13. The method of claim 11 further comprising (i) calculating an average pixel value for each intersection line based on stored values of pixels thereon and (ii) defining voxels intersected by the intersection line based on the average pixel value.

14. A system for constructing a voxel-based representation of an anatomical structure, the system comprising:
(a) a register for storing a plurality of images of the anatomical structure;
(b) a processor configured to (i) define a space of voxels, each having a size, with respect to the anatomical structure, (ii) determine a distance between the images, (iii) based on the determined distances and the voxel size, create a sufficient number of interpolated images between the stored images such that a sufficient number of voxels between the images are intersected by pixels from at least one image or interpolated image, and (iv) assign values to the voxels based on the intersecting pixels; and
(c) a display for displaying a three-dimensional representation of the anatomical structure constructed from voxels.

15. The system of claim 14 wherein the plurality of images comprises two-dimensional ultrasound images.

16. The system of claim 14 wherein the plurality of images comprises one-dimensional image lines.

17. The system of claim 14 wherein the plurality of images are registered to a reference coordinate system about the anatomical structure, the reference coordinate system establishing relative physical locations of the voxels.

18. The system of claim 17 wherein the voxel size corresponds to an average length of the voxel along each of three dimensions in the reference coordinate system.

19. The system of claim 14 wherein the processor is further configured to remove one or more of the plurality of images such that all voxels are intersected by at no more than one image.

20. The system of claim 14 wherein the processor is further configured to create two or more sub-images from each image in the series and performing processing steps (iii) through (v) using the sub-images.

* * * * *